United States Patent [19]

Zollinger et al.

[11] Patent Number: 4,707,543

[45] Date of Patent: Nov. 17, 1987

[54] PROCESS FOR THE PREPARATION OF DETOXIFIED POLYSACCHARIDE-OUTER MEMBRANE PROTEIN COMPLEXES, AND THEIR USE AS ANTIBACTERIAL VACCINES

[75] Inventors: Wendell D. Zollinger, Silver Spring; John Boslego, Rockville; Ellen Moran, Wheaton; Brenda Brandt, Gaithersburg; Hugh Collins, Largo, all of Md.; Robert Mandrell, Novato, Calif.; Patricia Altieri; Sanford Berman, both of Silver Spring, Md.

[73] Assignee: The United States of America as represented by the Secretary of the Army, Washington, D.C.

[21] Appl. No.: 777,068

[22] Filed: Sep. 17, 1985

[51] Int. Cl.⁴ ........................ C07K 3/24; C07K 15/04
[52] U.S. Cl. .................................. 530/402; 530/403; 530/350; 530/412; 530/418; 530/419; 530/420; 530/422; 530/825; 424/88; 424/92; 435/849; 435/851; 435/871; 435/875
[58] Field of Search .................... 424/88, 92; 435/849, 435/851, 871, 875; 530/350, 402, 403, 825, 412, 418–420, 422

[56] References Cited

U.S. PATENT DOCUMENTS

| 4,185,090 | 1/1980 | McIntire | 424/92 |
| 4,356,170 | 10/1982 | Jennings et al. | 530/395 |
| 4,372,883 | 2/1983 | Matuhashi et al. | 424/88 |
| 4,451,446 | 5/1984 | Vandevelde | 424/88 |
| 4,459,286 | 7/1984 | Hilleman et al. | 424/88 |
| 4,474,756 | 10/1984 | Mitsuhashi et al. | 530/351 |

OTHER PUBLICATIONS

Seid et al, JBC, 1981, pp. 7305–7310, Preparation and Characterization of Detoxified Lipapaleparcharide Protein Conjugate.

Primary Examiner—John Kight
Assistant Examiner—Garnette D. Draper
Attorney, Agent, or Firm—John H. Raubitschek; Francis A. Cooch; Werten F. W. Bellamy

[57] ABSTRACT

Process for preparing a detoxified polysaccharide-outer membrane protein complex from bacterial envelopes; the so-obtained products which are useful as vaccines against infection by the same bacteria and method for protecting animals against the same infection by administration of a pharmaceutical composition containing the detoxified polysaccharide-outer membrane protein complexes.

33 Claims, 7 Drawing Figures

4,707,543

PROCESS FOR THE PREPARATION OF DETOXIFIED POLYSACCHARIDE-OUTER MEMBRANE PROTEIN COMPLEXES, AND THEIR USE AS ANTIBACTERIAL VACCINES

BACKGROUND OF THE INVENTION

This invention relates generally to a process for the preparation of immunogenic detoxified polysaccharide-outer membrane protein complexes from bacteria and more particularly to the use of said complexes, as vaccines, to protect animals against infections by the bacteria from which it has been derived comprising administering to an animal a pharmaceutical composition containing the detoxified polysaccharide-protein complexes.

The virulence of certain gram-negative bacteria is enhanced by the presence of a capsule which envelopes the outer membrane and is made up of different components among which are polysaccharides and lipopolysaccharides.

The outer membrane proteins of gram-negative bacteria such as *Haemophilus influenza* type b, *Neisseria gonorrhoeae, Escherichia coli, Pseudomonas aeruginosa,* and *Neisseria meningitidis* have been shown to induce bactericidal antibodies in man, both when encountered in the course of natural infections and when given as a vaccine in which the proteins are noncovalently complexed to the capsular polysaccharide. Vaccines of this type, as exemplified by *Neisseria meningitidis,* have been studied by several groups to determine their potential for providing protection against group B meningococcal disease. In most instances the outer membrane proteins from a serotype 2a strain have been used together with group B polysaccharide. Although vaccines of this type have shown promise in terms of safety and immunogenicity, there are a number of problems which need to be resolved.

When presented as a complex with the outer membrane proteins, the B polysaccharide induces a transient IgM antibody response. These antibodies are bactericidal with rabbit complement, but have little if any bactericidal activity with human complement. This fact together with reports that antibodies to group B polysaccharide cross-react with human fetal and neonatal brain antigens suggest to applicants that these antibodies are probably not protective and an alternative to group B polysaccharide is needed in future vaccine preparations.

A second problem is the great antigenic diversity and variability of the outer membrane proteins. Meningococci possess multiple outer membrane proteins which are known to vary antigenically from strain to strain. According to the classification scheme of Tsai, et al. described in the *Journal of Bacteriology,* Volume 146, pages 69 to 78, 1981, 5 major classes of outer membrane proteins are recognized. Of these, classes 1, 2, 3, and 5 have been shown to vary antigenically from strain to strain. In addition, lipopolysaccharides are present and exhibit antigenic variability. From the point of view of vaccine development this creates problems both in terms of vaccine formulation and evaluation of the antibody response to vaccination. The number of different serotype proteins that can safely be included in a single vaccine may be limited by reactogenicity resulting from the residual lipopolysaccharide (LPS) associated with them and probably also by reactogenicity intrinsic to the proteins themselves.

Applicants have evaluated the human bactericidal antibody response to serotype 2b and serotype 15 outer membrane proteins, prepared these proteins relatively free of LPS (less than 1%), and discovered the immunogenicity and safety of these proteins when combined in a single vaccine and solubilized by the tetravalent mixture of A, C, Y, and W135 polysaccharides.

The existence of other methods for preparing vaccines useful against infections caused by gram-negative bacteria are disclosed in U.S. Pat. Nos. 4,451,446; 3,636,192; 3,859,434; 4,356,170; 4,123,520 and 3,978,209 which are hereby incorporated herein by reference.

Although partially effective vaccines are available for treatment of bacterial infections, most vaccines presently known to be employed have limited effectiveness.

SUMMARY OF THE INVENTION

This invention relates to a novel means for affording treatment and control of infections in animals, including human beings and other mammalian species, which may be caused by gram-negative bacteria. It is based upon the use or administration of immunogenically effective amounts of a detoxified polysaccharide-outer membrane protein complex against infection by the same bacteria from which it has been derived. The term "polysaccharide" as used herein includes lipopolysaccharides and capsular polysaccharides.

DETAILED DESCRIPTION OF THE PREFERRED EMBODIMENTS

Figure 1:
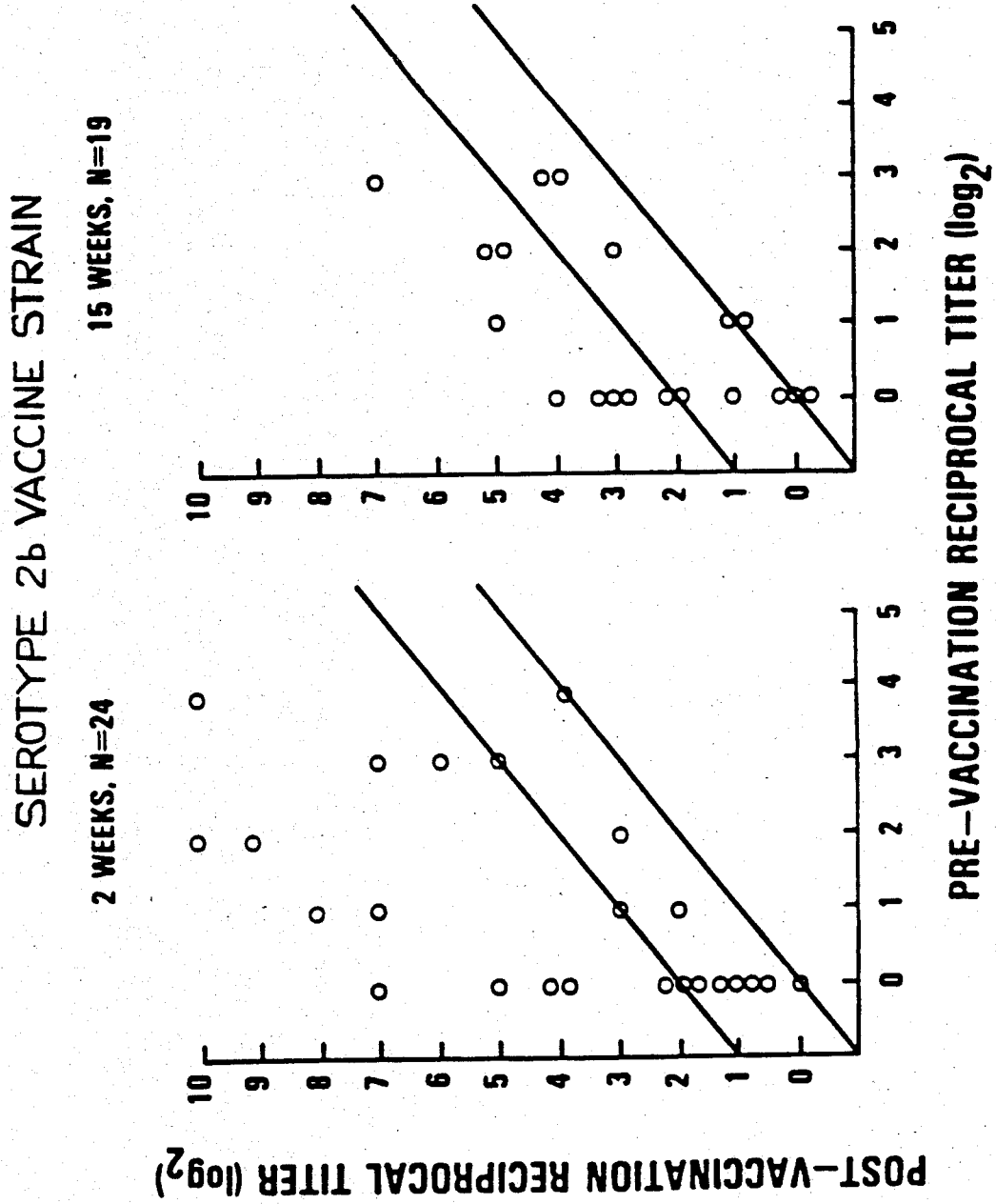
FIG. 1. Bactericidal titers against strain 8047 of pre- and post-vaccination sera from volunteers who were vaccinated with ACYW2b15-2. Only sera from volunteers who were non-carriers are included. The diagonal lines represent no response (lower line) and a four-fold increase (upper line). Several volunteers were no longer available at 15 weeks. Exogenous human complement (25%) was used, and an end point of 50% reduction in colony forming units was used.

Practical utility has been established for immunogenic detoxified polysaccharide-outer membrane protein complexes prepared from bacteria wherein the complex, unlike the bacteria from which it was derived, is essentially free (less than 1%) of toxic polysaccharide comprising the steps of:

a. suspending the outer membrane proteins in a buffer solution (TEEN) containing 1% of the zwitterionic detergent Empigen BB, 0.01M ethylenediaminetetraacetic acid (EDTA) 0.05M tris-HCl, and 0.15M NaCl, said solution having a pH of about 8.0;

b. stirring the suspension formed in step a. for about 1 hour at about room temperature followed by mild sonication;

c. centrifuging the suspension formed in step b. at about 20,000×g for about 15 minutes and separating the supernatant fluid from the insoluble residue;

d. adding solid ammonium sulfate to the supernatant layer formed in step c. in an amount of 500 grams/liter of supernatant protein solution and stirring until the ammonium sulfate is dissolved, and then allowing to stand at about room temperature for about 1 to 2 hours to allow precipitation of the outer membrane protein;

e. centrifuging the product of step d. at about 20,000×g for about 20 minutes and collecting the precipitated outer membrane proteins which form a top layer;

f. dissolving the precipitated outer membrane proteins formed in step e. in a buffer solution of the type described in step a. adding ammonium sulfate, and separating the precipitate;

g. repeating the process of step f.;

h. dissolving the precipitate formed in step g. in a TEEN buffer to form a solution, then dialyzing said solution against TEEN buffer to remove $(NH_4)_2SO_4$;

i. centrifuging the solution formed in step h. at about 35,000×g for about 20 minutes and removing any insoluble material;

j. filtering the solution formed in step i. sequentially through 1.2μ, 0.45μ, and 0.22μ membrane filters;

k. sterile filtering the solution formed in step j. through a 0.22μ membrane filter;

l. complexing the sterilized outer membrane proteins with the sterile filtered polysaccharide by combining the outer membrane protein, derived from one or more strains, and polysaccharide, derived from one or more strains, in a ratio within the range of 1:2 to 2:1 in TEEN buffer and coprecipitating by the cold, sterile absolute ethanol to 75% volume/volume;

m. centrifuging under sterile conditions, the ethanolic solution formed in step 1. at about 20,000×g for about 15 minutes and separating the precipitate.

n. washing the precipitate formed in step m. with sterile absolute ethanol to remove essentially all components of the buffer solution yielding an immunogenic detoxified polysaccharide-protein complex.

The immunogenic detoxified polysaccharide-protein complexes prepared in accordance with applicants' novel process are preferably stored in distilled water or a 3% lactose solution at about −20° C. for future use, although other physiologically-acceptable solvents can be used for this purpose.

Applicants' novel process is applicable to the preparation of detoxified lipopolysaccharide-outer membrane protein and capsular polysaccharide-outer membrane protein complexes wherein the lipopolysaccharide is noncovalently bonded the protein whereas capsular polysaccharides can be either bonded noncovalently or covalently to the protein to form a complex.

The process of this invention is generally applicable to the preparation of detoxified polysaccharide-protein complexes derived from gram-negative bacteria. Although bacteria such as *Neisseria meningitidis* group B, *Haemophilus influenza* type b, *Neissera gonorrhoeae, Escherichia coli,* and *Pseudomonas aeruginosa* are preferred.

Applicants have found that the outer membrane proteins which are referred to in step a. of their process can be in the form of an outer membrane complex, outer membrane vesicles or an extract from whole cells. When in the form of whole cell extract(s), the outer membrane proteins are first extracted from whole cells by the process comprising suspending said cells in a 0.15M NaCl solution, separating said cells from the solution by centrifugation at between 10,000 to 20,000×g for about 20 minutes and suspending the resulting cells in one volume of 1M sodium acetate buffer, pH 5.5, adding 9 volumes of 3% Empigen BB in 0.5M $CaCl_2$ and stirring for about 1 hour, adding ethanol to 20% volume/volume, centrifuging at about 20,000×g for about 10 minutes to separate the precipitate from the supernatant, adding ethanol to the supernatant to a final concentration of about 45% volume/volume, collecting the precipitate by centrifugation, dissolving the collected precipitate in a buffer solution containing 1% Empigen BB, 0.05M tris-HCl, 0.01M ethylenediaminetetracetic acid (EDTA), and 0.15M NaCl, said buffer solution having a pH of about 8.0 and separating of any insoluble material by centrifugation to yield an aqueous solution from which the outer membrane proteins are separated.

The outer membrane proteins referred to in step a. of applicants' process may be derived either from several different bacterial strains or a single bacterial strain. Applicants have found that the detoxified complexes prepared according to the process of this invention are most efficacious when the ratio between the polysaccharide and the outer membrane protein components of the complex are with the range 1:2 to 2:1, most preferably 1:1.

The sequential steps involved in applicants' process can be illustrated in the following schematic diagram I:

SCHEMATIC DIAGRAM I

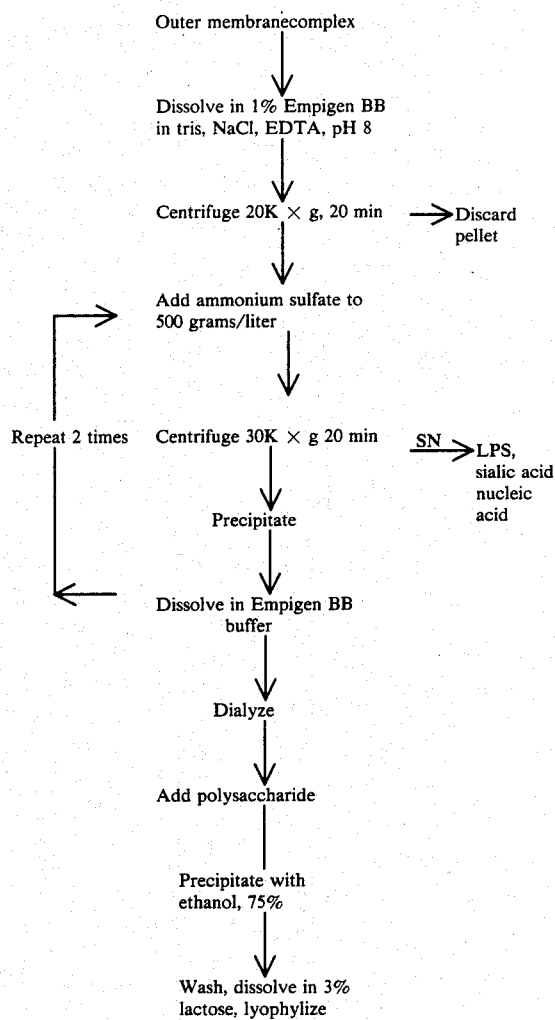

WORKING EXAMPLES

The working examples set forth below illustrate the preparation of representative compositions, but in no way limit the scope of the invention.

EXAMPLE 1

Noncovalent Complex of *Neisseria meningitidis* Group B Outer Membrane Proteins and Tetravalent Mixture of Capsular Polysaccharides A. Purfication of outer membrane protein from outer membrane complex.

Meningococci of serotype 2b (or 15) are grown in liquid culture (15 liters) under conditions which result in a heavy stationary state culture. The culture is inactivated with phenol at 0.5% for two hours and the organisms collected by centrifugation. Outer membrane complex is extracted from the organisms by the method of Zollinger, et al. (J. Clin. Invest. 63:836) and stored at −20° C. in distilled water.

The outer membrane complex is precipitated by addition of 2M NaCl to a final concentration of 0.15M and 2.5 volumes of absolute ethanol. The precipitate is collected by centrifugation at 8000×g for 15 minutes and the supernatant thoroughly drained off and discarded.

The pellets are dissolved in TEEN buffer which contains, 0.05M Tris-hydrochloride, 0.01M EDTA (ethylenediaminetetraacetic acid, disodium salt), 0.15M NaCl, and 1% of the zwitterionic detergent Empigen BB (Albright and Wilson, LTD., Whitehaven, England), pH 8.0. Alternatively the outer membrane complex may be mixed 1:1 with a 2X solution of the TEEN buffer. Solubilization is aided by mild sonication such as may be obtained by holding the flask in a bath sonicator. The solution is centrifuged at 30,000×g for 15 minutes and the supernatant collected. The pellets are resuspended in the TEEN buffer using a syringe and needle, sonicated briefly, and recentrifuged as above. The supernatants are pooled.

Solid ammonium sulfate is added to the solution in the amount of 500 g/liter and the mixture stirred until all the ammonium sulfate is dissolved. The solution is allowed to stand at room temperature for 1 hour and then centrifuged at 20,000×g for 20 minutes. The precipitated protein collects at the top of the tube and is recovered by drawing off the liquid from the bottom. Lipopolysaccharide, capsular polysaccharide, and nucleic acid remain in solution. When all the liquid is removed, the protein is redissolved in the TEEN buffer.

The precipitation with ammonium sulfate is repeated twice with the centrifugation being done when all the ammonium sulfate is dissolved. The final precipitate is dissolved in TEEN buffer at 1-2 mg/ml and dialyzed against 4 changes of 20 volumes of TEEN buffer to remove the ammonium sulfate. After dialysis the solution is centrifuged at 35,000×g for 20 minutes and then filtered sequentially through membrane filters with pore sizes of 1.2 μm, 0.45 μm, and 0.22 μm. The solution is then sterile filtered through a 0.22 μm filter and stored at −30° C.

After two precipitations with ammonium sulfate the protein contains about 1-3% residual lipopolysaccharide. After the third precipitation, residual LPS is at 1% or less, capsular polysaccharide is not detectable, and nucleic acid is less than 1%. The ammonium sulfate precipitated proteins are easily soluble in the TEEN buffer.

Polyacrylamide gel electrophoresis of the proteins by the method of Laemmli (Nature 227:680-685) and staining with coomassie brilliant blue shows the presence of two or three major bands corresponding to the class 1, class 2 (or 3), and class 5 major outer membrane proteins as classified by Tsai and Frasch (J. Bacteriol. 146:69-78). These proteins constitute about 70-90% of the total protein in the sample.

B. Preparation of the Polysaccharide-protein complex.

Purified capsular polysaccharides are prepared by the methods approved by the Office of Biologics, Food and Drug Administration and the World Health Organization for the currently licensed meningococcal polysaccharide vaccines. These methods are based on those of Gotschlich (U.S. Pat. No. 3,636,193). A mixture of equal amounts of the capsular polysaccharide from serogroups A, C, Y, and W-135 is dissolved in 0.15M NaCl at 1 mg/ml total polysaccharide. This solution is combined with an equal volume of TEEN buffer and sterile filtered through a 0.22 μm filter.

The sterile filtered capsular polysaccharides are combined at 4° C. with a mixture of equal amounts of sterile filtered outer membrane proteins from strains of two different serotypes. The amounts of polysaccharide and protein are calculated based on assays performed after the filtration, and are measured to give approximately equal amounts of total polysaccharide and total portein. In the present example a ratio of 3 parts polysaccharide to 2 parts protein was used. Three volumes of cold, sterile absolute ethanol are added to precipitate the mixture and remove the components of the TEEN buffer. The precipitate is collected by centrifugation at 16,000×g for 15 minutes and washed three times with cold, sterile absolute ethanol. The final precipitate is suspended in a solution of 3% lactose and constitutes the bulk product. It is stored at −30° C. until sterility is assured and then dispensed into glass vials and lyophilized.

The product is reconstituted with sterile saline for injection.

C. Immunological characteristics of the polyvalent polysaccharide-protein complex.

The final product (ACYW2B15-2) was evaluated for its antigenic activity by examining its ability to react with monoclonal antibodies against the serotype specific determinants of the major outer membrane proteins in a solid phase radioimmunoassay (Infect. Immun. 18:424–433). Antibodies to the serotype proteins of the serotype 2b and 15 strains were inhibited 50% by a concentration of 0.45 and 1.1 μg protein/ml, respectively. Antibodies to the class 1 protein were inhibited by 7.6 and 27.3 μg protein/ml.

Further immunological evaluation was done by immunizing Balb/C mice with this vaccine and the tetravalent capsular polysaccharide vaccine (ACYW). The results are given in Table A. One μg of protein (ACYW2b15-2) or 2 μg of polysaccharide (ACYW) was given intraperitoneally to groups of 6 mice at day 0 and day 21. The antibody levels were measured by SPRIA using outer membrane complex from the vaccine strains as antigen for anti-protein antibodies and poly-L-lysine followed by purified capsular polysaccharide as antigen for anti-polysaccharide antibodies. A good antibody response to the protein was observed which included a strong booster response to the dose given at 21 days. The antibody response to the capsular polysaccharides was enhanced somewhat in the protein-containing vaccine.

This vaccine has also been tested in rabbits with similar results for the protein antigens, but the rabbits did not respond to the capsular polysaccharides.

Several additional characteristics of the vaccine war given in Table B. About 50% of the polysaccharide was actually bound hydrophobically to the protein as determined by gel filtration on a column of Sepharose 4B-CL and comparing to a similar column run with polysaccharide alone. Some of the polysaccharide appears to lack a hydrophobic moiety necessary for binding to the proteins. The product was nonpyrogenic in rabbits at a dose of 0.1 μg/kg. The complexes were of high molecular weight with 90% of the polysaccharide eluting with a Kd of greater than 0.5.

EXAMPLE 2

Safety and Antigenicity Test of Polyvalent Protein-Polysaccharide Vaccine in Human Volunteers A noncovalent complex of outer membrane proteins (serotypes 2b and 15) and a tetravalent mixture (groups A, C, Y, and W-135) of capsular polysaccharide has been tested for safety and antigenicity in 65 adult volunteers. Such a vaccine if fully effective might protect against meningococcal disease of all 5 pathogenic serogroups (A, B, C, Y, and W-135). The composition on a dose basis of the vaccine lot tested is given in Table C. The protein used in this lot was only precipitated twice with ammonium sulfate (see Example 1) and, therefore, contains about 2% residual lipopolysaccharide. A single dose was given subcutaneously in the upper arm. The volunteers were mostly military recruits who routinely receive a licensed tetravalent meningococcal capsular polysaccharide vaccine. This vaccine was given by needle and syringe to a control group.

The vaccine appeared safe in that no severe or unusual reactions occured. A summary of reactogenicity is given in Table D.

The antiobody response to the protein antigens was measured by bactericidal assays against several different group B strains including the vaccine strains, 8047 and 44/76. Antibodies were also measured using an enzyme linked immunosorbant assay (ELISA). Seroconversions with respect to the group B vaccine strains are summarized in Table E. The geometric mean increase in bactericidal antibody to the homologous group B vaccine strains at two weeks is given in Table F along with the geometric mean increases determined by ELISA. Analysis of the bactericidal antibody response is shown in FIGS. 1 to 7.

Lower responses were seen when the sera were tested against heterologous serotypes. This suggests that much of the antibody is directed against serotype specific determinants and that it is important to prepare the vaccine outer membrane proteins from the most prevalent group B serotypes serotype(s).

EXAMPLE 3

Preparation of Outer Membrane Protein-detoxified lipopolysaccharide noncovalent complexes A. Preparation and Characterization of Detoxified Meningococcal LPS.

Lipopolysaccharide is purified (less than 1% nucleic acid and 1% protein) by standard methods such as the hot phenol-water method of Westphal, et al. (Z. Naturforsch, Teil B 7:148–155) from a serogroup B case strain e.g. 8047 or 44/76.

Purified lipopolysaccharide is detoxified by dissolving at about 4 mg/ml in 0.1N NaOH and placing the vessel in a 60° C. water bath for 3 hours. The reaction is stopped by addition of sufficient acetic acid to neutralize the NaOH and five volumes of cold absolute ethanol are added to precipitate the lipopolysaccharide. The precipitate is collected by centrifugation and washed twice with cold ethanol dissolved in distilled water and dialyzed against 100 volumes of distilled water overnight at 4° C. The solution is then lyophilized.

The biological and chemical properties of the detoxified lipopolysaccharide were studied and compared to native lipopolysaccharide. Gas liquid chromatographic analysis of fatty acid composition showed complete loss of ester linked fatty acids and retention of amide linked fatty acids. The relative toxicity of the native and detoxified product is compared in Table G. Four different toxicity tests were used and in each case a greater than 1000-fold decrease in toxicity was observed. A four log reduction in activity in the Limulus ameobocyte lysate gelation assay was also observed. No loss in antigenic determinants could be detected by binding of lipopolysaccharide-specific monoclonal antibodies in a spot blot assay. In addition, the detoxified product was shown to retain its ability to bind to and solubilize outer membrane proteins.

B. Preparation of Outer Membrane Protein-detoxified lipopolysaccharide complexes.

Detoxified lipopolysaccharide is dissolved in TEEN buffer (see Example 1) and sterile filtered through a 0.22 μm filter. This solution is combined with an equal amount of purified outer membrane protein from the group B strain 44/76 (B:15:P1.16:L3,8) also solubilized in TEEN buffer. Four volumes of cold, sterile absolute ethanol is added to coprecipitate the mixture. The precipitate is collected by centrifugation and washed three times as described in Example 1. The final precipitate is dissolved in sterile distilled water with the aid of mild sonication using a bath sonicator. Sonication is often essential to facilitate the protein-lipopolysaccharide interaction and solubilize the protein. The solubilized product is centrifuged at 10,000×g for 10 minutes to remove any insoluble material and the supernatant dispensed into vials and lyophilized. The product is reconstituted with normal saline for injection.

C. Immunological properties of detoxified lipopolysaccharide-outer membrane protein complexes.

Groups of 10 mice were vaccinated with a 1 μg (protein) dose of vaccine on days 0 and 28. Separate groups of mice were vaccinated with capsular polysaccharide (group C)-outer membrane protein complexes prepared using the same protein preparation [OMP(c)] and a different protein preparation from the same strain [OMP(b)]. Antibody levels against the homologous proteins were determined by solid phase radioimmunoassay using outer membrane complex as antigen. The results as given in Table H show that the outer membrane protein has approximately equivalent antigenicity when solubilized with either the detoxified lipopolysaccharide or the capsular polysaccharide. A strong antibody response to both the initial dose and the booster dose was observed.

EXAMPLE 4

Extraction of Meningococcal Outer Membrane Protein from Whole Cells

Meningococcal cells of strain 44/76 (B:15:P1.16:L3,8) are harvested from liquid culture by centrifugation at about 16,000×g for 20 minutes. The cells are suspended in about an equal volume of 1M sodium acetate buffer pH 5.5, and nine volumes of a solution containing 3% Empigen BB in 0.5M calcium chloride are added. The mixture is stirred at room temperature for one hour after which ethanol is added to a concentration of 20% volume/volume. The resulting precipitate is removed by centrifugation at about 20,000×g for 10 minutes. The pellets are discarded and the supernatant is brought to 45% ethanol volume/volume. The precipitated proteins are collected by centrifugation at about 20,000×g for 10 minutes and dissolved in buffer containing 1% Empigen BB, 0.15M NaCl, 0.01M EDTA, and 0.05M Tris-HCl at pH 8.0. Any insoluble material is removed by centrifugation at about 20,000×g for 10 minutes. The proteins are further purified to remove lipopolysaccharide, capsular polysaccharide, and nucleic acid by ammonium sulfate precipitation three times as described in Example 1A. This product gives essentially the same band pattern on SDS polyacrylamide gels as outer membrane protein purified from outer membrane complex or outer membrane vesicles. The purified outer membrane protein is noncovalently complexed with capsular polysaccharide or detoxified lipopolysaccharide as described in Examples 1 and 2.

Mice were vaccinated with complexes prepared from protein purified by this method [OMP(c)]. The procedure is given in Example 3C and the results in Table H. The antibody response obtained in mice with vaccines containing (OMP(c) are equally as good as those containing OMP(b) which was derived from outer membrane complex rather than whole cells.

TABLE A

Immunogenicity of Meningococcal Polyvalent Polysaccharide - Protein Vaccine in Mice

| Vaccine | Day | 8047 OMC | 44/75 OMC | Bsss | Asss | Csss | Ysss | Wsss |
|---|---|---|---|---|---|---|---|---|
| ACYW2b15-2 | 0 | .33* | .23 | .36 | .16 | .57 | .52 | .40 |
|  | 5 | 5.0 | 3.54 | .86 | 20.84 | 4.49 | 2.90 | 1.66 |
|  | 21 | 9.71 | 5.02 | .51 | .53 | 1.00 | 1.78 | .74 |
|  | 28 | 79.62 | 62.95 | .55 | 3.32 | 4.45 | 11.04 | 1.94 |
| ACYW | 0 |  |  |  | .30 | .50 | .39 | .32 |
|  | 5 |  |  |  | 1.37 | 1.96 | 1.50 | .86 |
|  | 21 |  |  |  | .58 | .82 | 1.24 | .57 |
|  | 28 |  |  |  | .84 | 1.36 | 2.14 | .76 |

*μg Antibody/ml by solidphase radioimmunoassay
Bsss = group B capsular polysaccharide, etc.

TABLE B

Characterization of Meningococcal Vaccine lot ACYW2b15-2

| Parameter | Result |
|---|---|
| Polysaccharide bound to protein (est.) | 51% |
| Rabbit pyrogen test | 0.12 μg/kg passed |
| Size of polysaccharide on Sepharose CL-4B+ | 90% with Kd > 0.5 |

+Based on sialic acid assay of column fractions.

TABLE C

Composition of Vaccine lot ACYW2b15-2

| Substance | μg/Dose ± 10% |
|---|---|
| Protein |  |
| (serotype 2b) | 60 |
| (serotype 15) | 60 |
| Polysaccharide |  |
| (group A) | 45 |
| (group C) | 45 |
| (group Y) | 45 |
| (group W-135) | 45 |
| Lipopolysaccharide* | 4.1 |
| Nucleic acid | 1.5 |
| Total+ | 305 |

+Based on assay of the bulk protein for KDO.
+In addition, the vaccine contained 4.8 mg lactose per dose and was reconstituted in normal saline (0.5 ml/dose).

TABLE D

Summary of Side Effects of Vaccine lot ACYW2b15-2 in Military Recruits at Ft. Benning, GA.

| | ACYW2b15-5 | ACYW |
|---|---|---|
| Number vaccinated | 54 | 47 |
| Question or complaint | Response-vaccine | Response-control |
| Temperature at 6–8 hr. | | |
| Geometric mean ± SEM | 37.31 ± 0.06 | 37.14 ± 0.07 |
| Mo. with temp. 37.8° C. | 3 | 1 |
| Mo. with temp. 37.6° C. | 9 | 5 |
| Erythema at 24 hr. (Geometric mean ± SEM of largest diameter in cm) | 3.76 ± 0.32 | 1.38 ± 0.25 |
| Number positive | 44/54 | 23/47 |
| Induration Number positive | 36 | 10 |
| Sore arm (Mean soreness index ± SEM scale of 0 to 4) | 1.57 ± 0.11 | 1.28 ± 0.15 |
| Number positive | 50 | 37 |

TABLE E

Seroconversions in Volunteers Vaccinated with Meningococcal Vaccines

| | | Percent seroconversion | | | |
|---|---|---|---|---|---|
| | | 8047(B:2b) | | 44/76(B:15) | |
| Vaccine | No. | ELISA | BCT | ELISA | BCT |
| ACYW2b15-2 | 54 | 91 | 66 | 94 | 76 |
| ACYW (Control) | 41 | 12 | 10 | 7.3 | 10 |

*Based on 4-fold or greater increase in bactericidal antibody (BCT), or 2-fold or greater increase in antibody in the ELISA.

TABLE F

Geometric Mean Antibody Response of Human Volunteers Vaccinated with Meningococcial Polyvalent Polysaccharide-Protein Vaccine ACYW2b15-2

| | | Geometric Mean Antibody Level at Indicated Time | | |
|---|---|---|---|---|
| Assay | Strain or Antigen | 0 wk | 2 wk | 14 wk |
| Bactericidal Assay | 8047(B:2b:P1.2) | 2.2 | 20.1 | 6.9 |
| | 44/76(B:15:P1.16) | 2.1 | 25.5 | 8.6 |
| ELISA Assay | 8047 OMC | 5.6 | 51.4 | 16.5 |
| | 44/76 OMC | 4.0 | 59 | 14.6 |

Only non-carriers are included in the data (N = 24). Values for the bactericidal test are reciprocal titers and those for the ELISA are μg IgG antibody/ml.

TABLE G

Characterization of Alkaline Detoxified Meningococcal Lipopolysaccharide*

| Property or Assay | Untreated LPS | Alkaline Treated LPS |
|---|---|---|
| Pyrogenicity in rabbits (μg/Kg) | Pyrogenic at 0.025 μg | Non-pyrogenic at 50 μg |
| Local Shwartzman reaction (μg for preparative dose) | Positive at 0.2 μg | Negative at 500 μg |
| Limulus lysate assay (Lowest positive conc.) | 1 ng/ml | 10 μg/ml |
| Chick embryo lethality test | $LD_{50}$ = < 1 μg | Non-toxic at > 1000 μg |
| Antigenic activity** | 0.2 μg/ml | 0.2 μg/ml |
| (Binding of monoclonal antibodies vs L8 & L3,7) | 1.6 μg/ml | 1.6 μg/ml |
| Capacity to bind to and solubilize OM protein | ++ | + |
| Galactosamine sensitized mouse toxicity Test ($LD_{50}$) | .003 μg | 3.3 μg |

*Lipopolysaccharide from strain 44/76 was treated with 0.1 N NaOH for 3 hr at 60° C.
**The lowest concentration of antigen that gave a positive reaction in a dot-blot assay with two different monoclonal antibodies to LPS.

TABLE H

Antibody Response of Mice to Meningococcal Outer Membrane Protein Noncovalently Complexed to Meningococcal Capsular Polysaccharide or Detoxified Lipopolysaccharide

| | Mean antibody response to OMP by SPRIA | | |
|---|---|---|---|
| Vaccine composition* | Day 0 | Day 28 (μg/ml) | Day 42 |
| OMP(b):C polysaccharide (1:1) | 0.40 | 27.8 | 1250 |
| OMP(c):C polysaccharide (1:1) | 0.48 | 22.5 | 910 |
| OMP(c):detoxified LPS (1:1) | 0.46 | 18.4 | 1175 |
| OMP(c):detoxified LPS (2:1) | 0.49 | 10.4 | 326 |
| Saline | ND | 0.87 | 1.7 |

*OMP(b) is outer membrane protein prepared from vesicles of outer membrane collected from the culture supernatant. OMP(c) is outer membrane protein extracted from whole cells by the method in Example 4. A serotype 15 strain 44/76(B:15:P1.16:L3,8) as used in each case for OMP and LPS.

UTILITY

The detoxified polysaccharide-outer membrane protein complexes prepared according to applicants' novel process of this invention induce immune response to bacterial infections. More specifically, evidence indicates that these complexes have activity against bacterial infections caused by gram-negative bacteria including *Neisseria meningitidis* group B, *Haemophilus influenza* type b, *Neissera gonorrhoeae*, *Escherichia coli*, and *Pseudomonas aeruginosa*.

Several experiments have been conducted to determine the activity of the detoxified polysaccharide-outer membrane protein complexes prepared according this invention. In order to guide one of ordinary skill in the practice of this invention, these experiments are described below, as well as results obtained in each experiment with a representative sampling of vaccine preparations.

PREPARATION AND CHARACTERIZATION OF LOW LPS VACCINES

Applicants' novel method for separating LPS from the outer membrane proteins was used to prepare several lots of vaccine which differed in formulation. This method which made use of the zwitterionic detergent Empigen BB, an alkyl betaine, (Albright and Wilson LTD, Cumbria, White Haven, UK), was compared to the previous method, described by Zollinger, et al., *Seminars in Infectious Disease,* Volume 4, "Bacterial Vaccines", pages 254–262, 1982; and Zollinger, et al., *Journal of Clinical Investigation,* Volume 63, pages 836 to 848, 1979, which involved preferential solubilization of LPS with sodium deoxycholate (DOC). The starting material in each case was outer membrane complex (OMC) prepared by one of several procedures. The essentials of the method include solubilization of the OMC in a buffer (TEEN) containing 1% Empigen BB, 0.05M tris-hydrochloride, 0.01M EDTA and 0.15M NaCl, pH 8.0 and thrice precipitating the protein with ammonium sulfate added as a solid to 500 g ammonium sulfate per liter of protein solution. The final precipitate was dissolved in TEEN and dialyzed against TEEN with 0.1% Empigen BB. For preparation of the vaccines, the protein was sterile filtered and complexed with polysaccharide as described by Zollinger, et al. in *Seminars In Infectious Disease,* Volume 4, "Bacterial Vaccines", pages 254 to 262, 1982.

Eight different lots of vaccine were prepared for use, characterized, and tested for safety and immunogenicity in animals; but because of the considerations mentioned above, only one lot, that did not contain the group B polysaccharide, was tested in human volunteers.

Several of these vaccines which differed in LPS content, method of preparation and composition are compared in Table 1. In experiment 1, vaccines which differed mainly in method of preparation were compared. Lot BP2b-1 was prepared by our previous method using deoxycholate to preferentially solubilize the LPS. Lot BP2b-2 was prepared from the same batch of OMC with the new Empigen BB method and contained about half as much LPS as lot BP2b-1. The geometric mean antibody response in mice as measured by solid phase radioimmunoassay (SPRIA) with homologous OMC as antigen was not significantly different.

In the second experiment, all three lots were prepared by the Empigen BB method. The protein in lot BP2b-3 was precipitated with ammonium sulfate three times and contained less than 1% LPS. It was compared to two other vaccines which contained protein that was precipitated twice with ammonium sulfate and contained about 3.5% residual LPS (relative to protein). Lot ACYW2b15-2 contained the tetravalent A, C, Y, and W135 polysaccharide mixture in place of the group B polysaccharide and the protein serotypes. Two doses of 0.5 g protein (1.0 g of lots ACYW2b15-2 and BP215-2) was given intraperitoneally at 0 and 21 days. Ten to twenty-fold geometric mean increases in antibodies were observed after both the initial dose and the booster dose. The results indicate that neither more complete removal of LPS nor replacement of the group B polysaccharide with the tetravalent A, C, Y, and W135 mixture adversely affected the immunogenicity of the serotype 2b protein. It is important to note that experiments one and two cannot be directly compared because the mice were about two months older (15 weeks versus 9 weeks) in the second experiment.

CHARACTERIZATION OF LOT ACYW215-2

Lot ACYW2b15-2 was chosen for human testing because it did not contain the group B polysaccharide, and because it had a formulation that was applicable to the needs of the military. Each dose of the vaccine contained 60 μg each of the serotype 2b and serotype 15 outer membrane proteins, 45 μg of each of the four capsular polysaccharides, about 4 μg of LPS and 1.5 μg of nucleic acid as shown in Table C. The total dose was approximately 300 μg. Further characteristics of this vaccine are given in Table 2. About 50% of the polysaccharide was bound to protein as estimated by the elution profile on Sepharose CL-4B compared to that of the purified polysaccharide mixture.

The vaccine was used to inhibit each of four murine monoclonal antibodies that were specific for determinants either on the serotype protein or the class one protein of the vaccine strains. The 2B strain had the P1.2 determinant on the class 1 protein and the serotype 15 strain had the p1.16 determinant on the class 1 protein. The results are given as the concentration required to inhibit 50% and were used as an identity test to demonstrate the presence of these specifid determinants in an antigenically active state. The vaccine passed the rabbit pyrogenicity test at a level of 0.12 μg/kg.

CLINICAL STUDIES

Vaccine lot ACYW2b15-2 was tested in 10 laboratory volunteers to insure safety and full immunogenicity of the tetravalent polysaccharide mixture. It was then tested for safety and immunogenicity in 54 recruit volunteers at Ft. Benning, GA. After obtaining informed consent, a single injection was given subcutaneously in the upper arm by needle and syringe. An additional 47 volunteers were given the regular tetravalent polysaccharide vaccine by needle and syringe as a control. Blood samples and throat cultures were obtained at 0, 2, 4, 6, 9, and 15 weeks. Temperatures were taken at 6 hours, and at 24 hours the vaccination site was examined and the individuals questioned regarding adverse reactions.

BACTERICIDAL ANTIBODY RESPONSE

The results reported here are limited to an analysis of the bactericidal antibody responses to the outer membrane protein portion of the vaccine. Since nasopharyngeal carriage of meningococci frequently leads to an increase in bactericidal antibodies, the data reported here, with several exceptions, are limited to those individuals who were noncarriers during the first 6 weeks of the study.

The bactericidal assays were performed in microtiter plates using 25% fresh human serum that lacked bactericidal activity against the test strain as an exogenous source of complement. The results were scored as a reduction in colony forming units after 60 minutes, and the titer was determined as the highest serum dilution that resulted in greater than a 50% reduction in colonies.

The pre- and post-vaccination antibody titers against the serotype 2b vaccine strain 8047 is shown in FIG. 1. At two weeks 66% of the volunteers had a 4-fold or greater rise in titer, and greater than 90% had at least at 2-fold rise. Of 12 individuals who lacked bactericidal antibody prior to vaccination, all but one acquired detectable bactericidal antibody at two weeks. By 15 weeks titers had decreased, but 70% were still above prevaccination levels.

Figure 2:
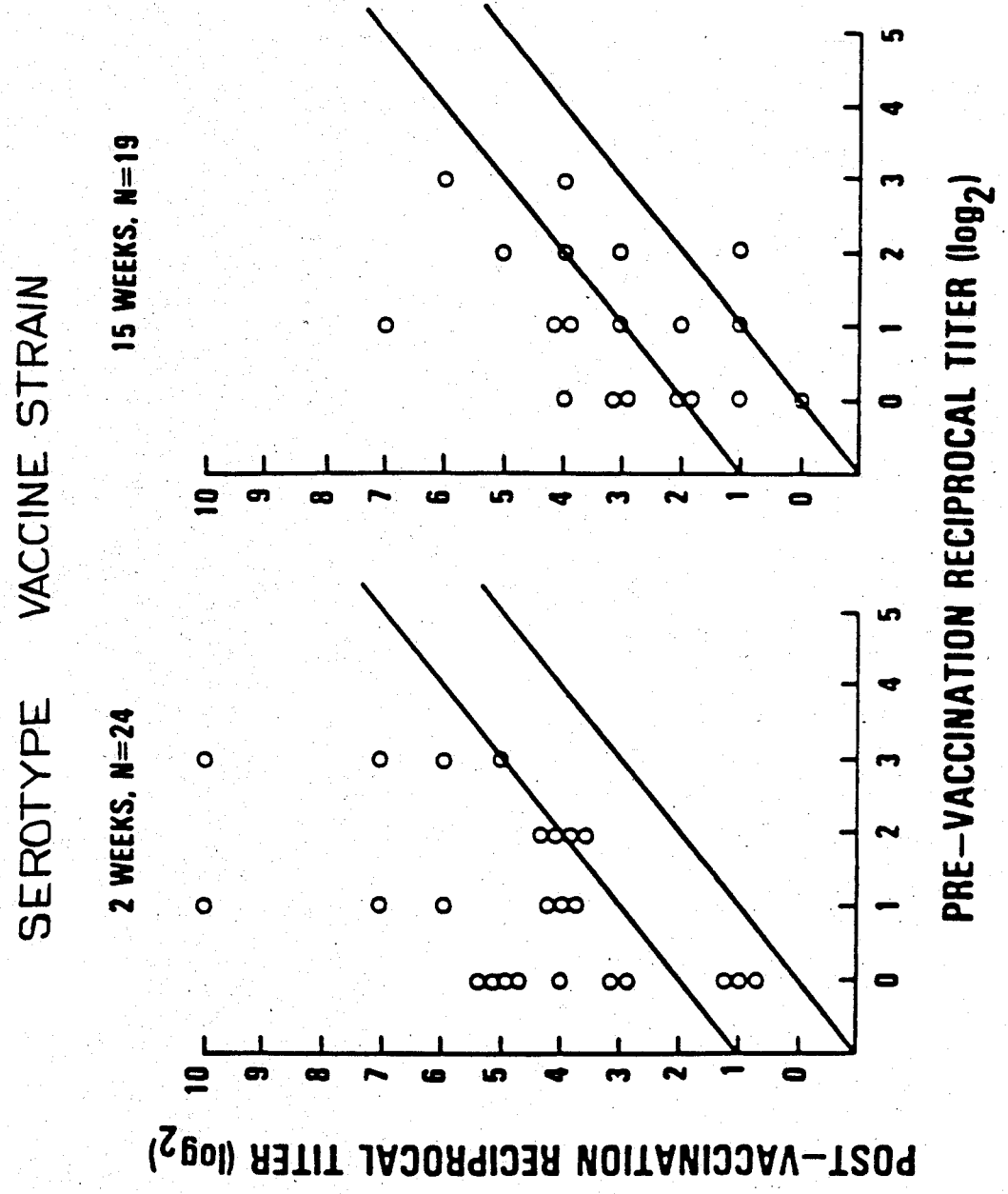
FIG. 2. Bactericidal titers against strain 44/76 of pre- and post-vaccination sera from volunteers vaccinated with ACYW2b15-2. See legend to FIG. 1 for assay conditions.

The bactericidal antibody titers to the serotype 15 vaccine strain, 44/76, were similar and are shown in FIG. 2. All but three had a 4-fold or greater rise in titer against this strain, and all had at least a two-fold rise. Again, at 15 weeks a few titers had returned to pre-vaccination levels, but about 85% remained at least 2-fold higher.

Figure 3:
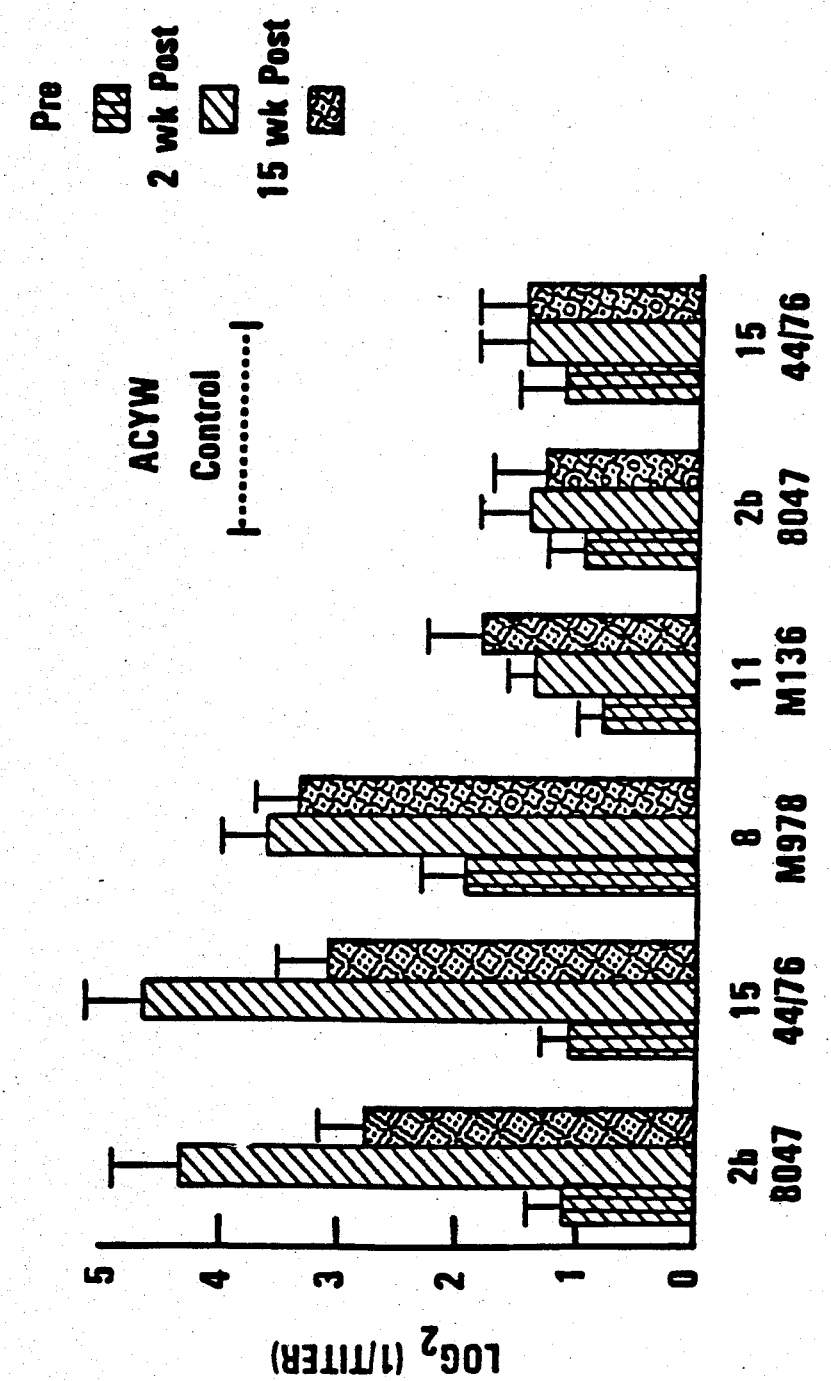
FIG. 3. Geometric mean bactericidal titers of pre- and post-vaccination sera against the vaccine strains 8047(B:2b:P1.2) and 44/76(B:15:P1.16) and two heterologous strains M978(B:8) and M136(B:11). Sera from 24 vaccinees (19 at 15 weeks) who received the ACYW2b15-2 vaccine and were noncarriers of meningococci were included. Sera from 21 noncarriers who received the control A,C,Y,W135 tetravalent polysaccharide vaccine were also tested against strains 8047 and 44/76.
Figure 4:
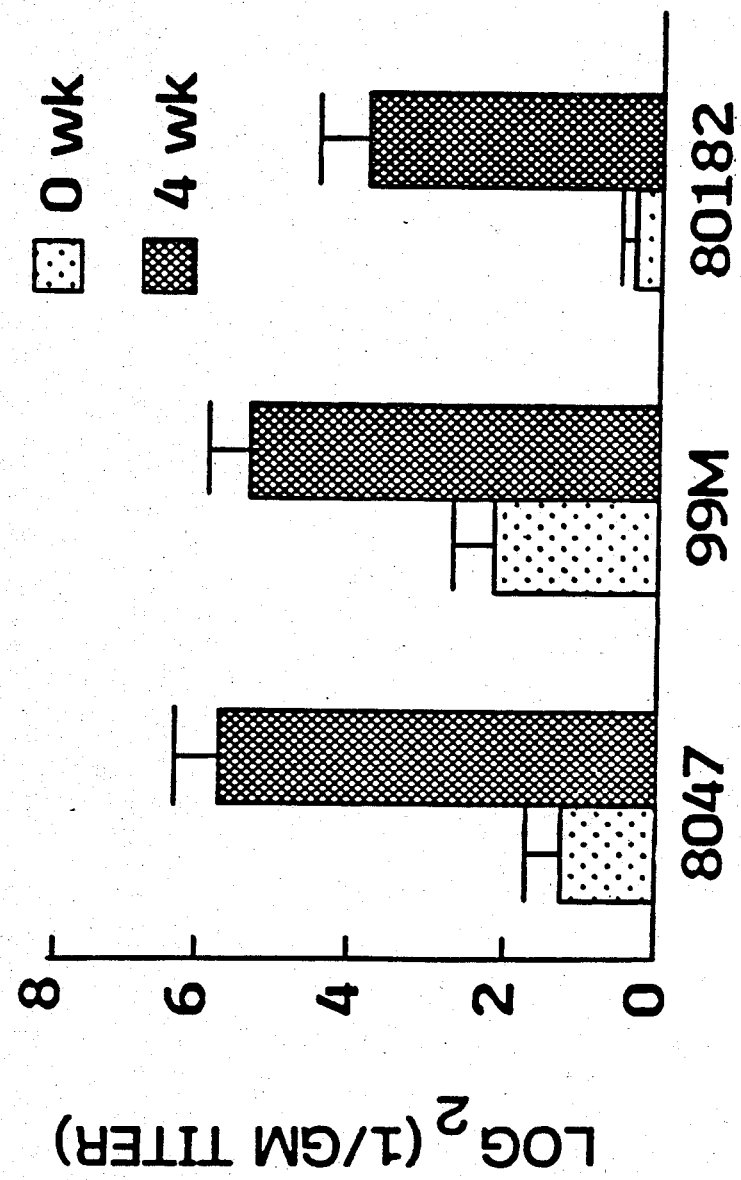
FIG. 4. Geometric mean bactericidal titers of ten pairs of pre- and post-vaccination sera from vaccinees who received the ACYWb15-2 vaccine. The sera were tested against one of the vaccine strains, 8047(B:2b:P1.2) and two related strains, 99M(B:2a:P1.2) and 80182(8:2b:P1-), one of which shares the class 2 serotype 2b determinant and one of which shares the class one protein determinant P1.2.

These same sera were also tested against two heterologous strains that shared neither the class 1 protein nor the serotype protein with either of the two vaccine strains. In FIG. 3 the geometric mean titers at 0, 2, and 15 weeks against the vaccine strains are compared to the titers against the two heterologous strains M978 (B:8) and M136 (B:11). The geometric mean bactericidal titers of controls who received the standard tetravalent A, C, Y, and W-135 polysaccharide vaccine and who were non-carriers are also given for comparison. Little or no increase in antibody to the serotype 11 strain was observed, but a significant, through reduced, increase was observed against the serotype 8 strain. An increase in the geometric mean of about 8-fold was observed against the two vaccine strains. These results suggest that although much of the bactericidal antibody is type specific, some cross reactive bactericidal antibodies are also induced.

To further investigate the specificity of the bactericidal antibodies, ten pairs of sera which showed a 4-fold or greater rise to one of the vaccine strains were tested against two heterologous strains, each of which shared ether the same serotype or the same class one protein type with the respective vaccine strain but not both. The geometric mean titer of these ten paired pre- and 4-week post-vaccination sera gainst the serotype 2b vaccine strain and two related strains are compared in FIG. 4. The serotype 2a strain, 99M, shares the class one protein with the vaccine strain and strain 80182 shares the serotype protein but has no detectable class 1 protein. The increase in titer against the two heterologous strains is less, but not much less, than against the homologous strain. Since both heterologous strains are killed about equally well, it appears that the bactericidal antibody is not predominantly directed against either the serotype protein or the class one protein.

Figure 5:
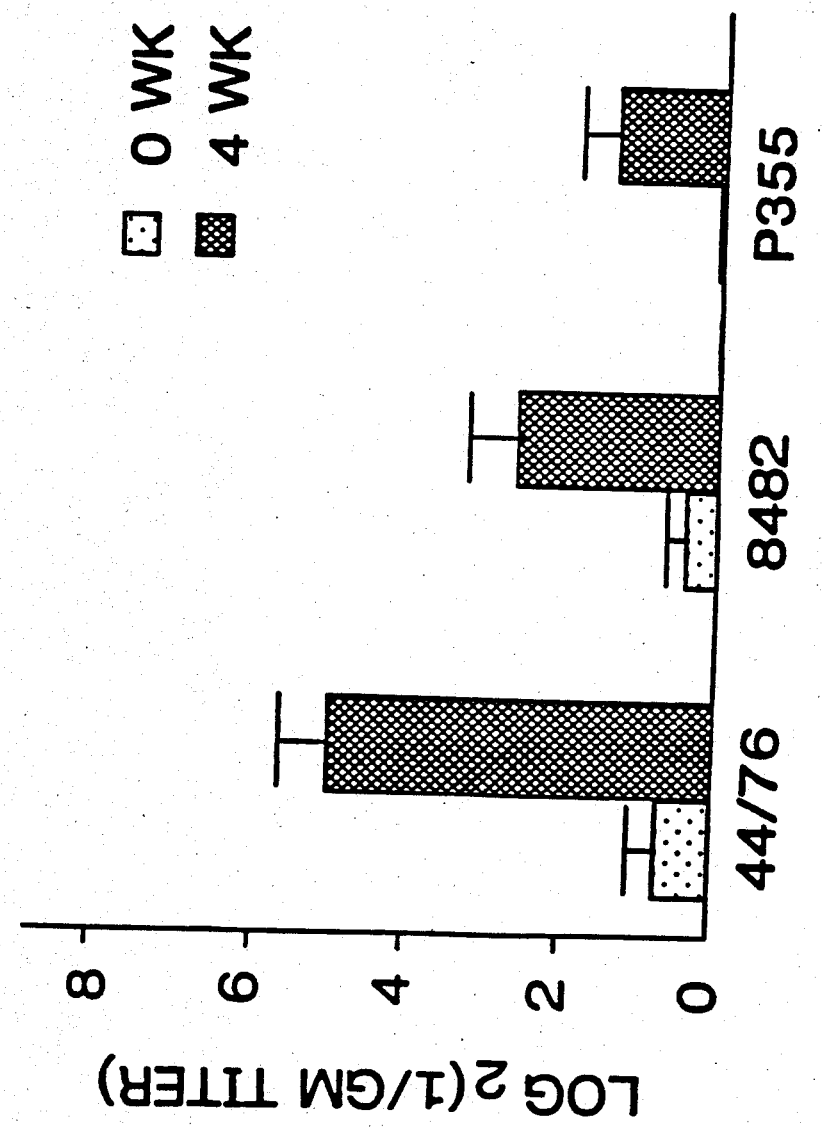
FIG. 5. Geometric mean bactericidal titers of ten pairs of pre- and post-vaccination sera from vaccines who received the ACYW2b15-2 vaccine. The sera were tested against on the vaccine strains, 44/76(B:15:P1.16), and two related strains, 8482(B:NT:P1.16) and P355(B:15:P1.15), one of which shares the class 3 serotype 15 determinant and one of which shares the class one protein determinant P1.16.
Figure 6:
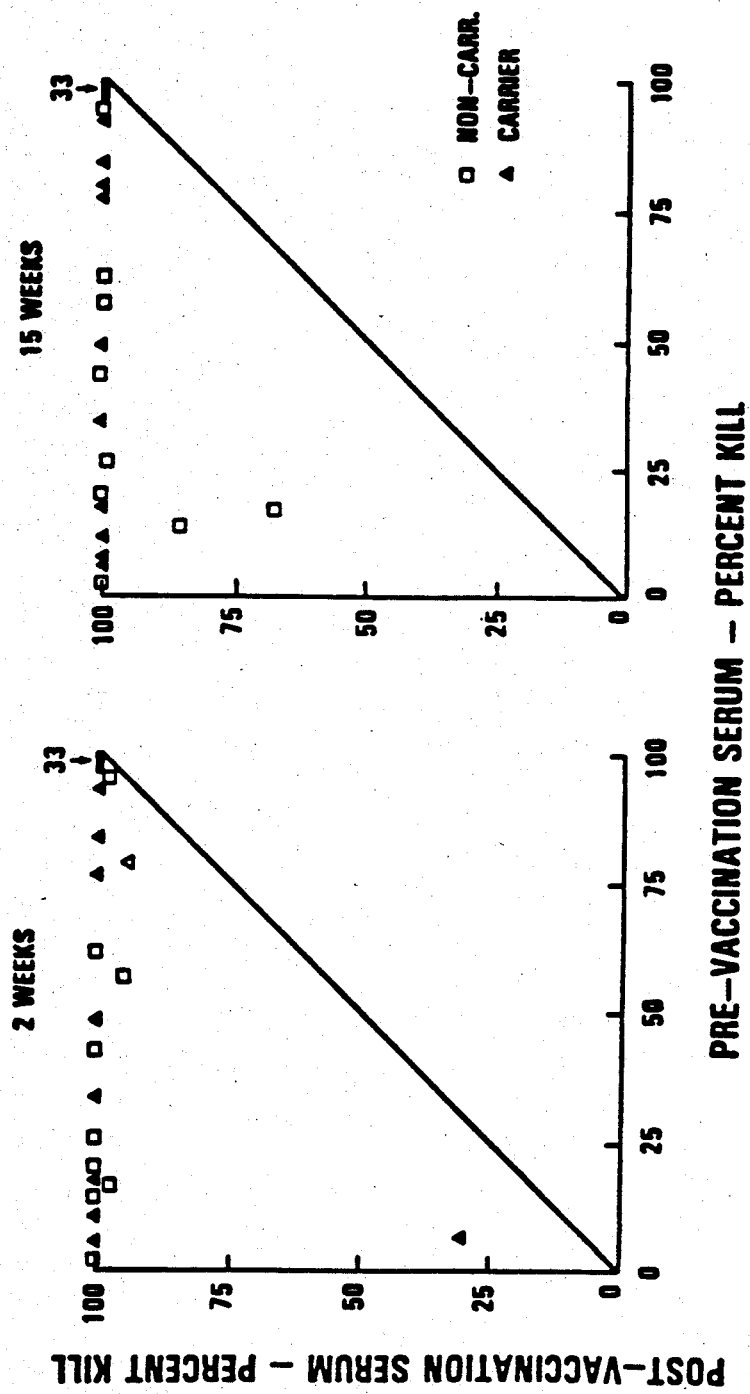
FIG. 6. Bactericidal activity of pre- and post-vaccination sera from 54 volunteers vaccinated with the vaccine ACYW2b15-2. Serum (not heat inactivated, stored at −70° C.) at a concentration of 50% was tested against a case strain, 8446(B:2b:P1.2), isolated at Ft. Benning, GA during the year preceeding the vaccine study. No exogenous complement was added.

A similar experiment was performed with the serotype 15 vaccine strain related strains (FIG. 5). In this experiment the geometric mean titer against strain 8242 which shared the class 1 protein was a little greater than against strain P355 which shared the serotype protein.

Since it was possible that the human serum that was used as a source of complement in the bactericidal assays might contain either blocking antibodies or natural antibodies that would augment the bactericidal activity of vaccine-induced antibodies, the bactericidal activity of fresh pre- and post-vaccination sera was determined without addition of exogenous complement. In these experiments, 50% fresh serum was combined with 25% bacteria and 25% buffer. The percentage decrease in colony forming units after 60 minutes at 37° C. was determined and compared to the control containing heat inactivated serum in place of fresh serum. The sera were tested against two recent group B case isolates that had been passed less than 4 times. The first (FIG. 6) was a serotype 2b strain which also shared the class 1 protein with the vaccine strain 8047. At two weeks all the sera but one were able to kill over 90% of the organisms. At 15 weeks all but two were still able to kill greater than 90%.

Figure 7:
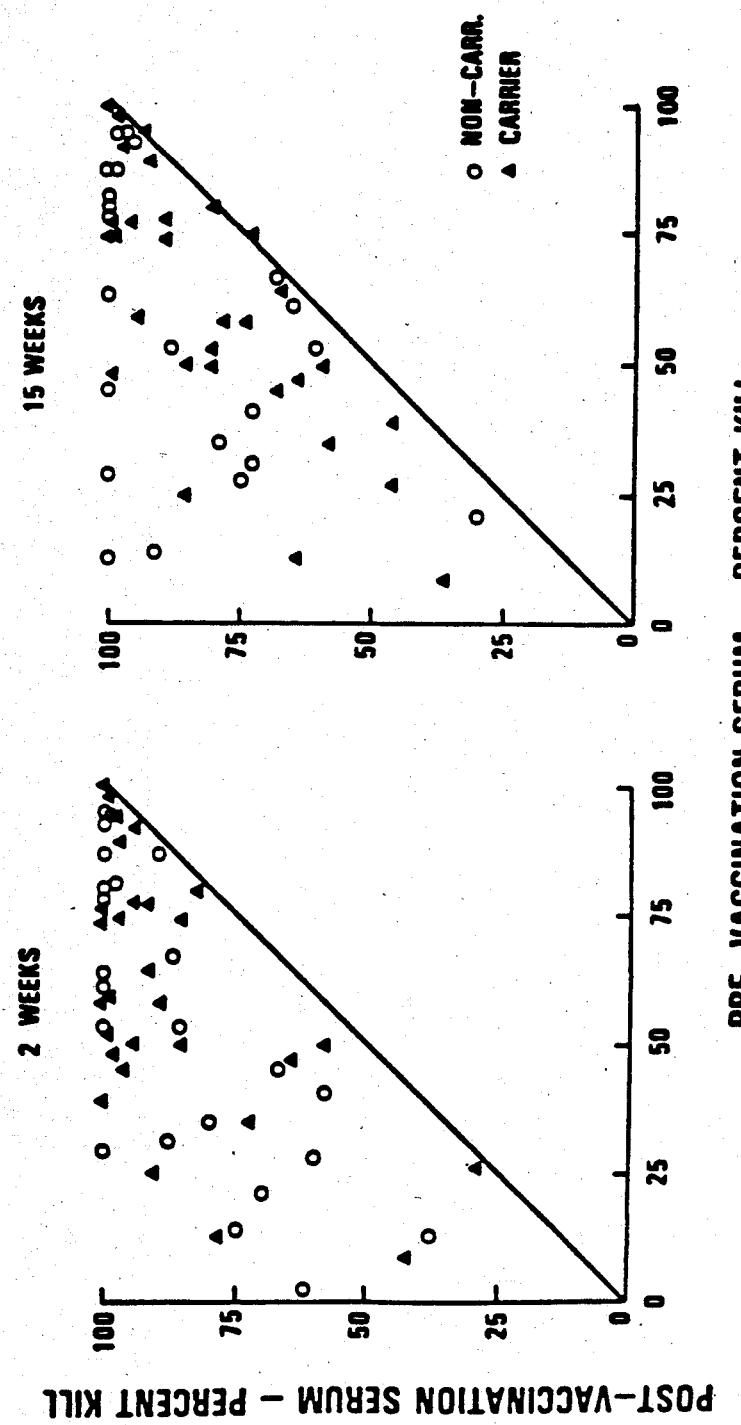
FIG. 7. Bactericidal activity of pre- and post-vaccination sera from 54 volunteers vaccinated with the vaccine ACYW2b15-2. Serum (not heat inactivated, stored at −70° C.) at a concentration of 50% was tested against a case strain, 8484(B:NT:P1.16), isolated at Ft. McClellan, LA in March 1984. No exogenous complement was added.

The second test strain was nontypable, but had the same class 1 protein type (P1.16) as the serotype 15 vaccine strain (FIG. 7). This strain was not killed as well by the post-vaccination sera as the serotype 2b strain. The 2-week sera of most individuals, however, showed an increase in bactericidal activity. All but three were able to kill greater than 50% of the organisms. By 15 weeks some had returned to pre-vaccination levels, but in many cases the antibody persisted through this period. These results support the concept that the bactericidal antibodies elicited by this type of vaccine will be functional in vivo in human beings.

SEROTYPING OF MENINGOCOCCI ISOLATED FROM MILITARY PERSONNEL

We were interested to know the percentage of cases of group B meningococcal disease that occurred in military personnel during the past 5 years that might have been prevented by use of a vaccine such as ACYW2b15-2. To answer this question we determined the serotype and class 1 protein type all of available group B case strains isolated from army personnel over the past 5 years. Monoclonal antibodies specific for the class 1 proteins and the serotype proteins of the two vaccine strains were used. In addition, serotype 2a and 2c-specific monoclonal antibodies were used. A simple spot-blot procedure 15 was used for serotype determination. The results indicated that most strains (58%) were serotype 2b with the P1.2 determinant on the class 1 protein. A single serotype 15 strain was present. Altogether, 65% of the isolates shared at least one major protein antigen with the vaccine strains. Of course this number would vary greatly with the population, time period and epidemiological setting.

The geometric mean bactericidal titers elicited by this vaccine were lower than those elicited by a previously tested vaccine which was a complex of serotype 2a outer membrane protein and group B polysaccharide prepared by the deoxychloate method. Although there are several possible explanations for this result, one possibility is that the amount of class 5 protein in the present vaccine was quite low. The vaccine strains were chosen with this intent because, although the class 5 proteins are known to be immunogenic in man, they exhibit a high degree of variability in their occurrence and antigenic specificty. Some evidence for this interpretation was obtained by testing ten pairs of sera from the previous study against the vaccine strain (99M) before and after passage of the strain in a guinea pig subcutaneous chamber (Table 3). The geometric mean titer of this set of sera dropped from 1:328 against the unpassed strain to 1:20 in the guinea pig passed variant. Several differences were identified between the two variants. After passage in the guinea pig the colonies were more opaque and one of two class 5 proteins present in the unpassed variant had disappeared. Thus, much of the high-titered antibody may have been directed against the missing class 5 protein.

TABLE 1

Comparison of Antibody Responses in Mice to Vaccines Prepared with Different Detergents and Having Different Compositions

| Vaccine | Expt. | PB bound mg/mg prot. | LPS mg/mg prot. | Antibody response in mice* | | | |
|---|---|---|---|---|---|---|---|
| | | | | Pre | 5 d | 21 d | 28 d |
| BP2b-1 (deoxycholate) | 1 | .35 | .07 | .29 | .35 | .59 | 8.25 |
| BP2b-2 (Empigen) | 1 | .36 | .03 | .25 | .32 | .81 | 14.5 |

TABLE 1-continued
Comparison of Antibody Responses in Mice to Vaccines Prepared with Different Detergents and Having Different Compositions

| Vaccine | Expt. | PB bound mg/mg prot. | LPS mg/mg prot. | Antibody response in mice* | | | |
|---|---|---|---|---|---|---|---|
| | | | | Pre | 5 d | 21 d | 28 d |
| BP2b-3 (Empigen) | 2 | .6 | .01 | .32 | 3.5 | 5.2 | 127 |
| BP2b15-2 (Empigen) | 2 | .53 | .034 | .37 | 2.6 | 4.6 | 70.3 |
| ACYW2b15-2 (Empigen) | 2 | .7 | .034 | .33 | 5 | 9.7 | 79.6 |

*Mice were vaccinated i.p. on day 0 and day 21 with 0.5 μg protein or 1.0 μg protein for lots containing both serotypes. Values are geometric mean μg antibody/ml vs serotype 2b OMC for groups of six Balb c/J mice as determined by SPRIA.

TABLE 2
Characterization of Meningococcal Vaccine Lot ACYW2b15-2

| Parameter | Result |
|---|---|
| Polysaccharide bound to protein (est.) | 51% |
| Antigenic activity of protein epitopes | MIC-50 (μg/ml)* |
| 2b | 0.45 |
| 15 | 1.1 |
| P1.2 | 7.6 |
| P1.16 | 27 |
| Rabbit pyrogen test | 0.12 μg/kg passed |
| Size of polysaccharide on Sepharose CL-4B+ | 90% with Kd > 0.5 |

*Amount of total protein required for 50% inhibition of monoclonal antibody binding in the solid phase radioimmunoassay.
+Based on sialic acid assay of column fractions.

TABLE 3
Effect of Passage in a Guinea Pig Subcutaneous Chamber on the Suseptibility of Strain 99 M to Human Complement-Mediated Bactericidal Activity by Paired Sera from 11 Recruits Vaccinated with Meningococcal Group B Vaccine

| Strain/Variant | Pre-Vaccination | | Post-Vaccination | |
|---|---|---|---|---|
| | Positive/Total | G. M. Titer | Positive/Total | G. M. Titer |
| 99 M/Unpassed | 6/11 | 1:4 | 11/11 | 1:328 |
| 99 M/G. P. Passed | 1/11 | 1:1.1* | 9/11 | 1:20 |

*Seronegative = 1

We claim:

1. A process for preparing an immunogenic detoxified polysaccharide-outer membrane protein complex from bacteria wherein said complex is essentially free of toxic polysaccharide comprising the steps of:
   a. suspending the outer membrane proteins in a TEEN buffer solution containing 1% of the zwitterionic detergent Empigen BB, 0.01M ethylenediaminetetraacetic acid, 0.05M tris-HCl, and 0.15M NaCl, said solution having a pH of about 8.0;
   b. stirring the suspension formed in step a. for about 1 hour at about room temperature followed by mild sonication;
   c. centrifuging the suspension formed in step b. at about 20,000×g for about 15 minutes and separating the supernatant fluid from the insoluble residue;
   d. adding solid ammonium sulfate to the supernatant layer formed in step c. in an amount of 500 grams/liter of supernatant protein solution and stirred until the ammonium sulfate is dissolved, and then allowed to stand at about room temperature for about 1 to 2 hours to allow precipitation of the outer membrane protein;
   e. centrifuging the product of step d. at about 20,000×g for about 20 minutes and collecting the precipitated outer membrane proteins which form a top layer;
   f. dissolving the precipitated outer membrane proteins formed in step e. in a buffer solution of the type described in step a., adding ammonium sulfate, and separating the precipitate;
   g. repeating the process of step f.;
   h. dissolving the precipitate formed in step g. in a TEEN buffer to form a solution, then dialyzing said solution against TEEN buffer to remove $(NH_4)_2SO_4$;
   i. centrifuging the solution formed in step h. at about 35,000×g for about 20 minutes and removing any insoluble material;
   j. filtering the centrifuged solution formed in step i. sequentially through 1.2μ, 0.45 μ, and 0.22μ membrane filters;
   k. sterile filtering the solution formed in step j. through a 0.22μ membrane filter;
   l. complexing the sterilized outer membrane proteins with a sterile filtered polysaccharide by combining the outer membrane protein, derived from one or more strains, and polysaccharide, derived from one or more strains, in a ratio within the range of 1:2 to 2:1 in TEEN buffer and coprecipitating by the cold, sterile absolute ethanol to 75% volume/volume;
   m. centrifuging, under sterile conditions, the ethanolic solution formed in step l. at about 20,000×g for about 15 minutes and separating the precipitate; and
   n. washing the precipitate formed in step m. with sterile absolute ethanol to remove essentially all components of the buffer solution yielding an immunogenic detoxified polysaccharide-protein complex.

2. The process according to claim 1 wherein the immunogenic detoxified polysaccharide-protein complex formed in step m. is dissolved in distilled water and stored at about −20° C.

3. The process according to claim 1 wherein the immunogenic detoxified polysaccharide-protein complex formed in step m. is dissolved in a 3% lactose solution and stored at about −20° C.

4. The process according to claim 1 wherein the polysaccharide-outer membrane protein complex is selected from the group consisting essentially of lipopolysaccharide-outer membrane protein complex and capsular polysaccharide-outer membrane protein complex.

5. The process according to claim 1 wherein the polysaccharide-outer membrane protein complex is a detoxified lipopolysaccharide-outer membrane protein complex.

6. The process according to claim 1 wherein the polysaccharide-outer membrane protein complex is a capsular polysaccharide-outer membrane protein complex.

7. The process according to claim 5 wherein the type of bacteria is gram-negative.

8. The process according to claim 7 wherein the bacteria is selected from the group consisting essentially of *Neisseria meningitidis* group B, *Haemophilus influenzae* type b, *Neissera gonorrhoeae, Escherichia coli,* and *Pseudomonas aeruginosa.*

9. The process according to claim 8 wherein the bacteria is *Neisseria meningitidis* group B.

10. The process according to claim 8 wherein the bacteria is *Haemophilus influenzae* type b.

11. The process according to claim 8 wherein the bacteria is *Neisseria gonorrohoeae.*

12. The process according to claim 8 wherein the bacteria is *Pseudomonas areuginosa.*

13. The process according to claim 8 wherein the bacteria is *Escherichia coli.*

14. The process according to claim 1 wherein the outer membrane proteins referred to in step a. are in the form of an outer membrane complex, outer membrane protein or extract from whole cells.

15. The process according to claim 14 wherein the outer membrane proteins of step a. are extracted from whole cells which comprises suspending said cells in a 0.15M NaCl solution, separating said cells from the solution by centrifugation at between 10,000 to 20,000×g for about 20 minutes and suspending the resulting cells in one volume of 1M sodium acetate, pH 5.5, adding 9 volumes of 3% Empigen BB in 0.5M $CaCl_2$ and stirring for about 1 hour, adding ethanol to 20% volume/volume, centrifuging at about 20,000×g for about 10 minutes to separate the precipitate from the supernatant, adding ethanol to the supernatant to a final concentration of about 45% volume/volume, collecting the precipitate by centrifugation, dissolving the collected precipitate in a buffer solution containing 1% Empigen BB, 0.05M tris-HCl, 0.01M ethylene diamine tetraacetic acid, and 0.15M NaCl, said buffer solution having a pH of about 8.0 and separation of any insoluble material by centrifugation to yield an aqueous solution from which the outer membrane proteins are separated.

16. The process according to claim 1 wherein the outer membrane proteins are derived from several different bacterial strains.

17. The process according to claim 1 wherein the outer membrane proteins are derived from a single bacterial strain.

18. The process according to claim 1 wherein the polysaccharide is derived from several different bacterial strains.

19. The process according to claim 1 wherein the polysaccharide is derived from a single bacterial strain.

20. The process according to claim 3 wherein the lipopolysaccharide-outer membrane protein complex is noncovalently bonded.

21. The process according to claim 4 wherein the capsular polysaccharide-outer membrane protein complex is covalently bonded.

22. The process according to claim 4 wherein the capsular polysaccharide-outer membrane protein complex is noncovalently bonded.

23. A process for purifying outer membrane protein derived from bacterial wherein said protein is essentially free of toxic polysaccharide comprising the steps of:

a. suspending the outer membrane proteins in a TEEN buffer solution containing 1% of the zwitterionic detergent Empigen BB, 0.01M ethylenediaminetetraacetic acid, 0.05M tris-HCl, and 0.15M NaCl, said solution having a pH of about 8.0;

b. stirring the suspension formed in step a. for about 1 hour at about room temperature followed by mild sonication;

c. centrifuging the suspension formed in step b. at about 20,000×g for about 15 minutes and separating the supernatant fluid from the insoluble residue;

d. adding solid ammonium sulfate to the supernatant layer formed in step c. in an amount of 500 grams/liter of supernatant protein solution and stirred until the ammonium sulfate is dissolved, and then allowed to stand at about room temperature for about 1 to 2 hours to allow precipitation of the outer membrane protein;

e. centrifuging the product of step d. at about 20,000×g for about 20 minutes and collecting the precipitated outer membrane proteins which form a top layer;

f. dissolving the precipitated outer membrane proteins formed in step e. in a buffer solution of the type described in step a., adding ammonium sulfate, and separating the precipitate;

g. repeating the process of step f.;

h. dissolving the precipitate formed in step g. in a TEEN buffer to form a solution, then dialyzing said solution against TEEN buffer to remove $(NH_4)_2SO_4$;

i. centrifuging the solution formed in step h. at about 35,000×g for about 20 minutes and removing any insoluble material;

j. filtering the centrifuged solution formed in step i. sequentially through $1.2\mu$, $0.45\mu$, and $0.22\mu$ membrane filters; and k. sterile filtering the solution formed in step j. through a $0.22\mu$ membrane filter thereby obtaining sterilized outer membrane proteins.

24. The process according to claim 23 wherein the bacteria is selected from the group consisting essentially of *Neisseria meningitidis* group B, *Haemophilus influenza* type b, *Neissera gonorrhoeae, Escherichia coli,* and *Pseudomonas aeruginosa.*

25. The process according to claim 24 wherein the bacteria is *Neisseria meningitidis* group B.

26. The process according to claim 24 wherein the bacteria is *Haemophilus influenza* type b.

27. The process according to claim 24 wherein the bacteria is *Neisseria gonorrohoeae.*

28. The process according to claim 24 wherein the bacteria is *Pseudomonas areuginosa.*

29. The process according to claim 24 wherein the bacteria is *Escherichia coli.*

30. The process according to claim 24 wherein the outer membrane proteins referred to in step a. are in the form of an outer membrane complex, outer membrane protein or extract from whole cells.

31. The process according to claim 30 wherein the outer membrane proteins of step a. are extracted from whole cells which comprises suspending said cells in a 0.15 M NaCl solution, separating said cells from the solution by centrifugation at between 10,000 to 20,000×g for about 20 minutes and suspending the resulting cells in one volume of 1 M sodium acetate, pH 5.5, adding 9 volumes of 3% Empigen BB in 0.5 M $CaCl_2$ and stirring for about 1 hour, adding ethanol to 20% volume/volume, centrifuging at about 20,000×g for about 10 minutes to separate the precipitate from the supernatant, adding ethanol to the supernatant to a final concentration of about 45% volume/volume, collecting the precipitate by centrifugation, dissolving the collected precipitate in a buffer solution containing 1% Empigen BB, 0.05 M tris-HCl, 0.01 M ethylene diamine tetraacetic acid, and 0.15 M NaCl, said buffer solution having a pH of about 8.0 and separation of any insoluble material by centrifugation to yield an aqueous solution from which the outer membrane proteins are separated.

32. The process according to claim 24, wherein the outer membrane proteins are derived from different bacterial strains.

33. The process according to claim 24 wherein the outer membrane proteins are derived from a single bacterial strain.

* * * * *